United States Patent [19]

Risk

[11] Patent Number: 5,346,677
[45] Date of Patent: Sep. 13, 1994

[54] INSTRUMENT CASSETTE

[76] Inventor: William B. Risk, 511 Valleyview La., Lafayette, Ind. 47905

[21] Appl. No.: 150,549

[22] Filed: Nov. 9, 1993

Related U.S. Application Data

[63] Continuation of Ser. No. 940,536, Sep. 4, 1992, abandoned.

[51] Int. Cl.⁵ .......................... A61L 2/00; B01L 9/00
[52] U.S. Cl. ....................... 422/297; 422/104;
422/300; 206/363; 206/369; 206/370; 206/438;
206/480; 206/565; 206/63.5; 211/4; 248/500;
433/79
[58] Field of Search ............... 422/104, 297, 300, 310;
206/210, 263, 363, 369, 370, 438, 480, 483, 565,
635; 211/4, 8, 7, 60.1, 64; 248/500, 510; 433/77,
79; 24/3 F; 269/126–128; 190/36

[56] References Cited

U.S. PATENT DOCUMENTS

| | | | |
|---|---|---|---|
| 2,147,510 | 2/1939 | Amick | 206/263 X |
| 4,135,868 | 1/1979 | Schainholz | 422/310 |
| 4,541,992 | 9/1985 | Jerge et al. | 422/300 |
| 4,774,063 | 9/1988 | Runnells | 422/297 |
| 4,854,475 | 8/1989 | Riihimaki et al. | 220/337 |
| 4,930,660 | 6/1990 | Porteous | 220/367 |
| 4,959,199 | 9/1990 | Brewer | 422/300 |
| 5,084,251 | 1/1992 | Thomas | 422/300 |
| 5,173,273 | 12/1992 | Brewer | 422/300 |

OTHER PUBLICATIONS

Alabama Instrument Management, Cassette Tray, A Complete One-Step Procedure Design Operatory to Ultrasonic Cleaner Direct to Sterilizer to Operatory, HSP, Booklet.

*Primary Examiner*—James C. Housel
*Assistant Examiner*—Milton I. Cano
*Attorney, Agent, or Firm*—McAndrews, Held & Malloy, Ltd.

[57] ABSTRACT

A cassette for the sterilization and storage of dental or medical instruments includes a lower tray and an upper cover hingeably joined together for pivotal movement between an open position and a closed position. Both the tray and the cover have instrument positioning racks mounted therein to position the instruments in side-by-side relation within the tray and the cover. The cover is provided with an instrument retainer for simultaneously retaining the instruments in the positioning racks in the tray and the cover when the cassette is in the closed position. The instrument retainer includes an instrument retaining bar pivotally mounted at one end thereof within the cover and releasably fastened at the other end thereof to the cover. A resilient retaining member is mounted on the retaining bar and transversely pressingly contacts the instruments to retain them in the positioning racks. The instrument retainer is removable so that it can be adjusted between a first position and a second, inverted position to permit the storage of larger sizes of instruments within the cassette.

19 Claims, 4 Drawing Sheets

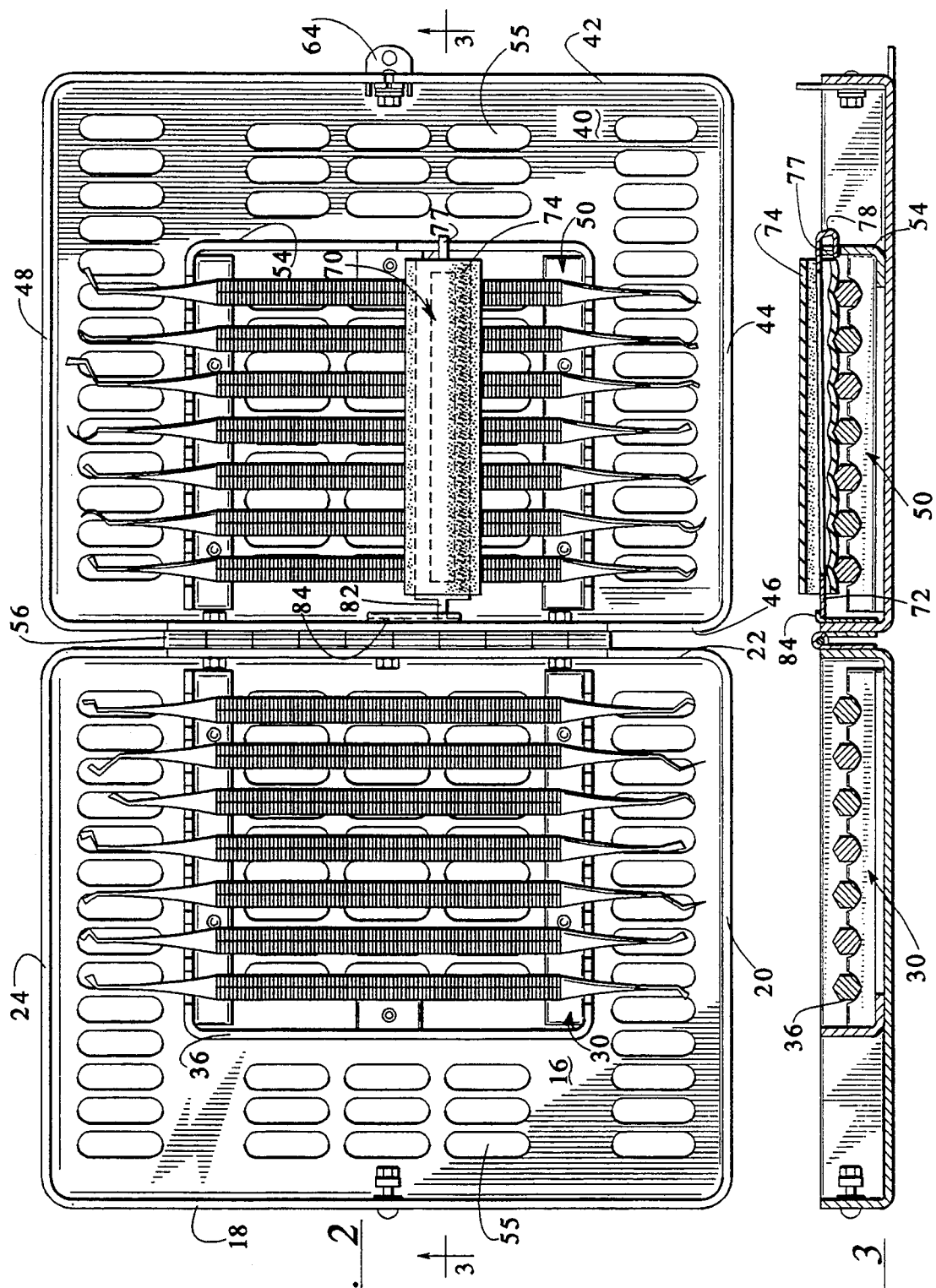

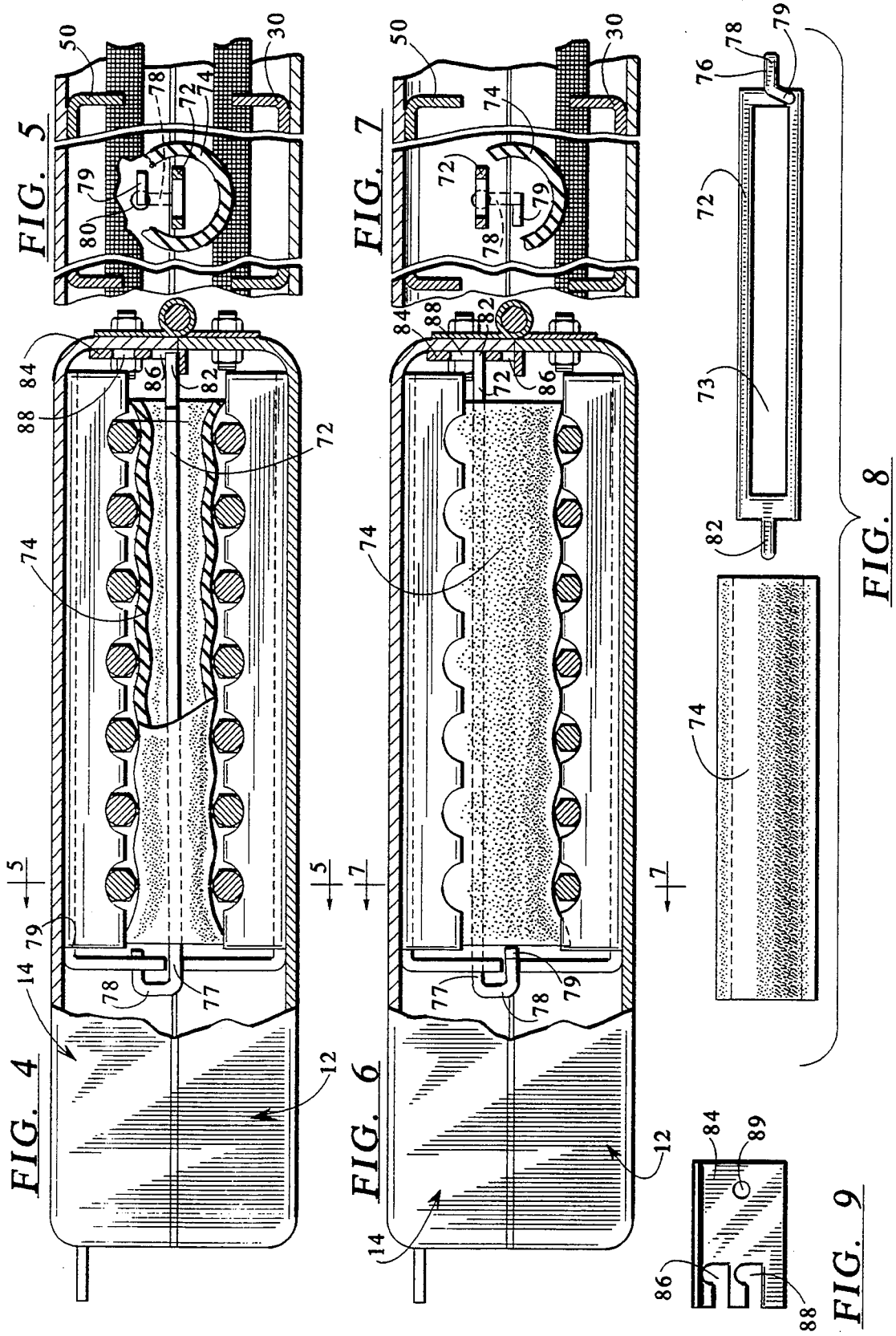

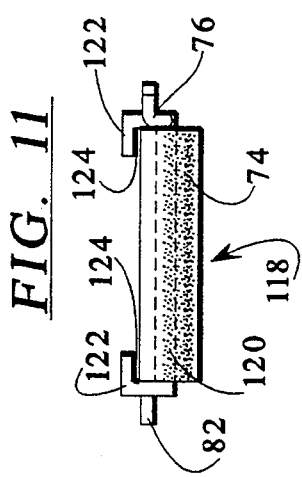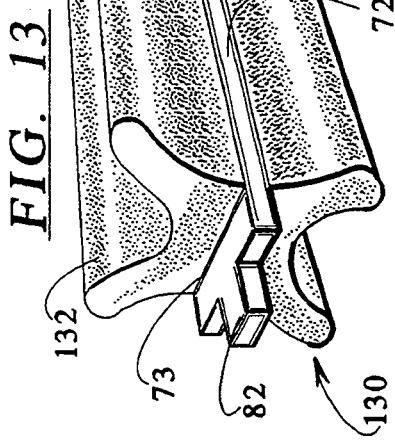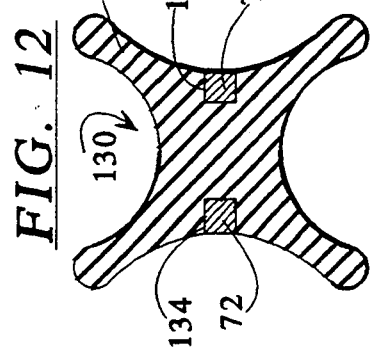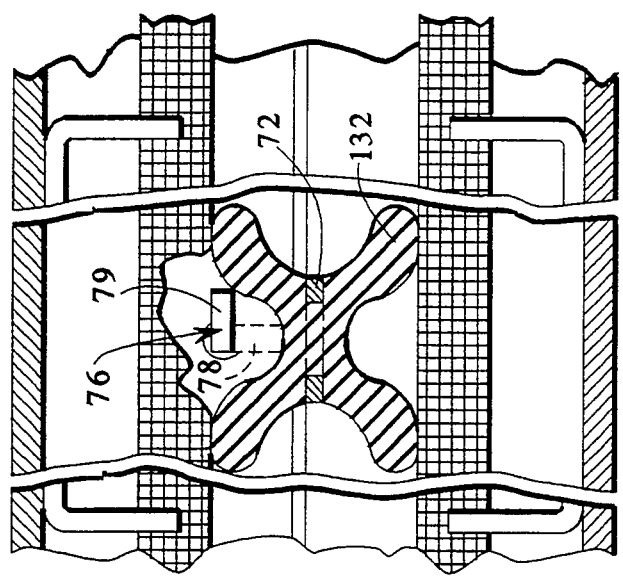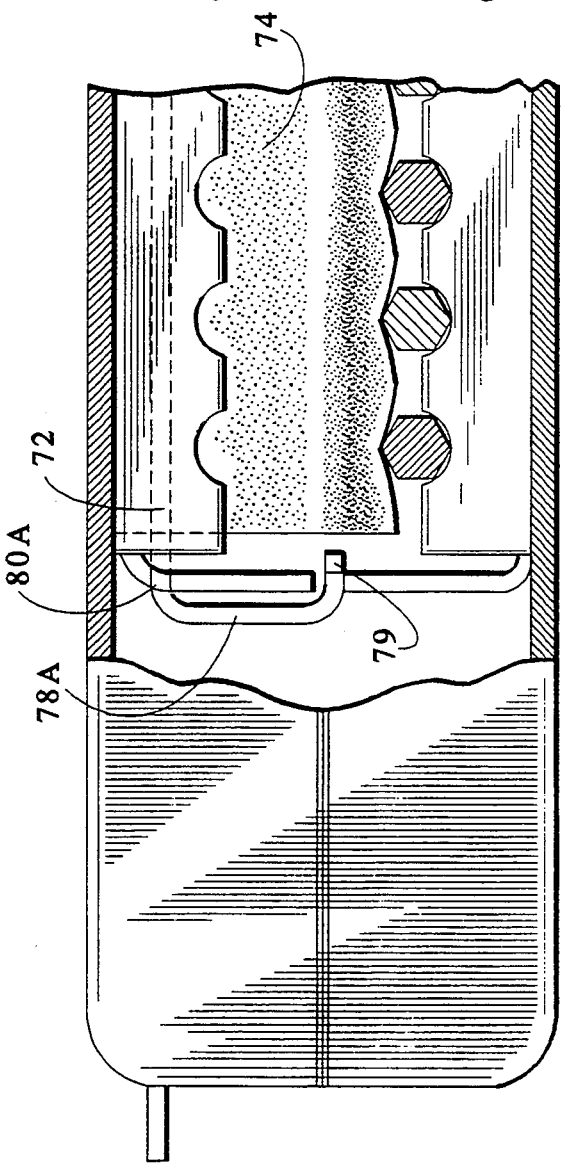

INSTRUMENT CASSETTE

This is a continuation of application Ser. No. 07/940,536, filed Sep. 4, 1992now abandoned.

BACKGROUND OF THE INVENTION

The present invention relates to trays for holding dental or medical instruments and, more particularly, to dental or medical instrument cassettes that permit the storage and sterilization of instruments.

Working trays or cassettes that store dental or medical instruments and permit their sterilization are known in the art. Such cassettes typically retain the instruments within instrument-holding notches for use during a procedure. After completion of the procedure, the cassette is closed and placed in an ultrasonic cleaner so that the contaminated instruments can be cleaned. After cleaning, the cassette (with its instruments) is rinsed, wrapped in an autoclave wrap, and then placed in an autoclave to sterilize the instruments. The cassettes are typically of a size and shape that permit stacking so that more than one cassette can be sterilized at the same time. Although larger, more expensive autoclaves that hold multiple cassettes are available, the autoclaves most commonly used by individual practitioners permits only a very small number of cassettes to be sterilized in one batch. With practitioners seeing up to 30 patients in one day, it becomes quite time-consuming to run many sterilization cycles of the autoclave and only sterilize a small number of instruments per cycle. Thus, there is a need in the field for an instrument cassette that permits greater efficiency in the sterilization process.

One way to increase efficiency is to reduce the size of the cassette so that more cassettes can fit in the autoclave. However the size of the cassette is often dictated by the number and size of the instruments that are needed for a procedure. Typically, 12–18 instruments are arranged side by side in the bottom tray of the cassette so that the cassette must be about 10–12 inches long in order to hold all the instruments.

One solution for decreasing the size of the cassette without decreasing its capacity is found in U.S. Pat. No. 4,930,660 to Porteous. That patent discloses an instrument cassette in which both the lower tray and the upper cover of the cassette are used for storing instruments. One advantage of this design is that the cassette can be smaller in size since the top half can accommodate half of the instruments. The instruments are held in place by the convolutions of a coil spring placed laterally across each cassette half. Although the coil spring is adequate for holding instruments of the same size, it cannot accommodate larger instruments, such as forceps, except at the risk of permanent deformation of the spring.

U.S. Pat. No. 4,854,475 to Riihimaki et al. discloses an instrument cassette that is provided with flexible, compressible instrument-retaining members that can receive medical or dental instruments of various shapes and sizes. The instruments are held in place by a flexible, compressible clamping member mounted to the lid of the cassette. Although the clamping member functions adequately to hold the instruments in place, two hands are required to manipulate the clamping member and remove it from the lid, making it cumbersome to use. Thus, there is also a need in the field for an instrument cassette that can hold instruments of various sizes and which has an instrument retaining member that can be easily manipulated.

SUMMARY OF THE INVENTION

An object of the present invention is to provide a stackable instrument cassette of relatively small dimension to permit more cassettes to be loaded into an autoclave for sterilization.

Another object of the invention is to provide an instrument cassette that will retain instruments of various sizes.

A further object of the invention is to provide an instrument cassette that includes an instrument retainer member that can retain instruments in both the upper and lower halves of the cassette and can be pivotally moved to lie flat in the upper half when not needed for instrument retention.

A still further object of the invention is to provide an instrument cassette that includes an instrument retainer member that is of relatively simple construction and that can be easily manipulated with one hand.

In a preferred embodiment of the invention an instrument cassette for holding and sterilizing medical or dental instruments comprises a lower tray and an upper cover hingeably joined together for pivotal movement between an open position and a closed position. The tray and the cover are each provided with an instrument positioning rack for positioning the instruments in side-by-side relation within the tray and the cover. The cassette further includes means disposed in the cover for retaining the instruments in the positioning rack in the cover. The retaining means comprises a retaining bar and a resilient retaining member mounted on the retaining bar. The retaining bar is pivotally mounted at one end thereof within the cover and has means at its other end for releasably fastening the bar to the cover. The retaining means is pivotable within the cover between a retaining position, in which it lies transverse of the instruments positioned within the positioning rack, and a non-retaining position, in which it is parallel to the longitudinal axis of the instruments. In the retaining position, the resilient retaining member is in pressing contact with the instruments in the cover when the retaining means is fastened to the cover. Preferably, the resilient retaining member is of sufficient size to also pressingly contact the instruments in the positioning rack in the lower tray when the cassette is in its closed position, so that a single retaining means may simultaneously retain all the instruments in the positioning racks in both the tray and the cover. In the non-retaining position, the retaining means is away from the instruments to permit easy access to the instruments during a procedure.

The fastening means for fastening the retaining bar to the cover preferably comprises a pin extending outwardly from the end of the bar. The pin is slidingly received by a horizontal slot provided on a plate mounted to the rear wall of the cover. The plate may have more than one horizontal slot to permit repositioning of the retaining means relative to the size of the instruments in the cassette. The pin is easily released from the horizontal slots by one-hand manipulation.

The retaining bar is advantageously releasably pivotally mounted to the cover so that the retaining bar can be removed from the cover and remounted inside the cover in an inverted position. In the inverted position, the resilient retaining member is in contact with the top wall of the cover so that larger sized instruments can be held in the tray portion. The pivotal mounting comprises a J-shaped hook that extends outwardly from the one end of the retaining bar. The end of the hook is inserted into an opening in the front wall of the positioning rack in the cover from either the front face of the wall or the rear face of the wall depending on the desired position for the retaining bar.

These and other aspects, objects and advantages of the invention are explained in a detailed description of the preferred embodiment of the invention, which accompanies the following drawings in which

BRIEF DESCRIPTION OF THE DRAWINGS

FIG. 2 is a top plan view of the instrument cassette of FIG. 1 in the open position;

FIG. 3 is a sectional view, taken along line 3—3 of FIG. 2;

FIG. 4 is a fragmentary side elevation of the instrument cassette of FIG. 1 in the closed position, showing the instrument retainer in a first position;

FIG. 5 is a sectional view taken along line 5—5 of FIG. 4;

FIG. 6 is a fragmentary side elevation of the instrument cassette in the closed position showing the instrument retainer inverted into its second position;

FIG. 7 is a sectional view taken along line 7—7 of FIG. 6;

FIG. 8 is an exploded view of the instrument retainer of FIG. 1;

FIG. 9 is an elevation view of the latch plate for the instrument retainer;

FIG. 10 is a fragmentary side elevation of the instrument cassette in the closed position showing a modified instrument retainer inverted into its second position;

FIG. 11 is top plan view of an alternative embodiment of the retaining bar of the instrument retainer.

FIG. 12 is a transverse cross-sectional view of an alternative embodiment of the resilient retaining member of the instrument retainer;

FIG. 13 is a perspective view of the alternative embodiment shown in FIG. 12;

FIG. 14 is a sectional view similar to that of FIG. 5, except showing the alternative embodiment of FIG. 12.

DETAILED DESCRIPTION OF THE PREFERRED EMBODIMENT

Figure 1:
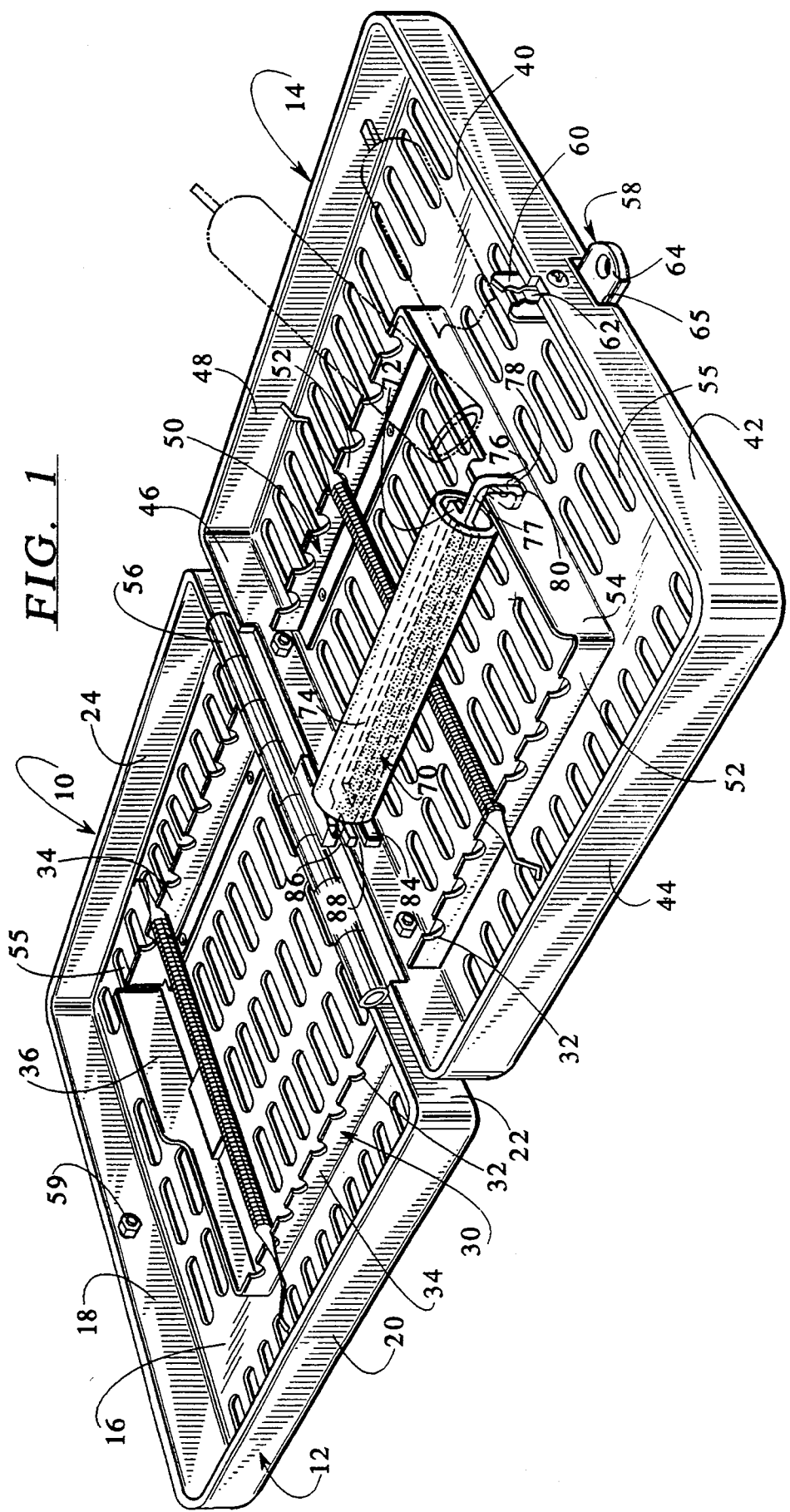
FIG. 1 is a perspective view of the instrument cassette of the invention in the open position, illustrating the pivotal movement of the instrument retainer in phantom.

Referring to FIGS. 1 and 2, a cassette for holding and sterilizing medical or dental instruments is generally indicated at 10. The cassette has a lower rectangular tray 12 and an upper rectangular cover 14 and is preferably made of metallic material, such as aluminum, stainless steel, or the like, so that it can withstand repeated cycling through a process of steam sterilization in an autoclave.

The lower tray 12 has a bottom wall 16 and four upstanding tray sidewalls 18, 20, 22 and 24 defining a tray interior. A lower instrument positioning rack 30 is mounted to the bottom wall 16 within the tray interior and has two parallel upstanding sidewalls 34 and an upstanding front wall 36. The sidewalls 34 are provided with a series of semi-circularly shaped grooves 32 aligned on each sidewall of the rack for receiving dental instruments, as shown in FIGS. 1 and 2. The side walls 34 and the front wall 36 of the positioning rack 30 are preferably smaller in dimension than the sidewalls of the tray to provide space for smaller auxiliary items, such as burrs, matrix retainers and the like, within the tray interior.

The upper cover 14 has a top wall 40 and four downwardly depending cover sidewalls 42, 44 46, and 48 defining a cover interior. An upper instrument positioning rack 50 is mounted to the top wall 40 within the cover interior and includes downwardly depending sidewalls 52 and a front wall 54. The sidewalls 52 are provided with aligned semi-circularly shaped grooves 32 for receiving dental instruments. Both the bottom wall 16 and the top wall 40 are perforated by a plurality of openings 55 to permit the sterilization steam from an autoclave to reach the interior of the cassette and the instruments in the positioning racks. Typical dimensions for the bottom tray and top cover are about 5-6 inches wide and 7-8 inches long so that several cassettes can be stacked to fit within an autoclave.

A hinge mechanism 56 mounted on the rear side wall 22 of the tray and the rear side wall 46 of the cover rotatably joins the tray to the cover so that the tray and the cover can move relative to each other from the open position, shown in FIGS. 1 and 2, to the closed position, shown in FIGS. 4, 6, 10 and 14.

A locking mechanism, comprising a locking arm 58 mounted to the inside of the front wall 42 of the cover and a locking stud 59 mounted to the inside of the front wall 18 of the tray, locks the cassette in the closed position. The locking arm has downwardly (in the closed position) depending legs 60 that form a circularly shaped restriction 62, and a tab portion 64 that is perpendicular to the legs and projects outwardly through an opening 65 at the juncture of the top wall 40 and the front wall 42. The restriction 62 is slightly smaller in diameter than the diameter of the locking stud 59 so that, as the tab portion is pushed downward, the legs 60 are slightly forced apart by and snap onto the locking stud, and the locking stud is releasably captured within the restriction 62.

Referring now to FIGS. 1-8, the instrument cassette of the present invention is provided with a novel instrument retainer 70 that functions not only to retain the instruments in the upper instrument positioning rack 50 as the cassette is moved between open and closed positions, but also to retain the instruments in the lower positioning rack 30 when the cassette is in the closed position. The instrument retainer comprises a flat, rectangularly shaped retaining bar 72 having a rectangularly shaped slot 73 therethrough, and a resilient hollow retaining member 74 mounted on the retaining bar. The resilient hollow retaining member has an inside diameter that is approximately the same distance as the width of the retaining bar so that the retaining member is slidably retained on the retaining bar. The retaining bar is preferably made of metallic material, such as aluminum, stainless steel, and the like. The resilient member 74 is formed from a flexible heat resistant material, such as silicone, capable of withstanding repeated cyclings in an autoclave.

The retaining bar is provided at one end with a hooked projection 76 for releasably pivotally mounting the instrument retainer 70 to the cover 14. As best seen from FIGS. 1 and 4-8, the hooked projection 76 is roughly J-shaped with a projecting tongue 79 at its end. More specifically, the projection 76 has a stem portion 77 that projects outwardly from the end of the bar in a direction coaxial with a central longitudinal axis extending through the bar, a curved portion 78 that is perpendicular to the stem portion 77 but is also coplanar with the stem portion and the central longitudinal axis of the bar 72, and the tongue 79, which extends outwardly from the curved portion 78 in a direction substantially perpendicular to the plane containing the central longitudinal axis of the bar 72. The instrument retainer 70 is mounted in the cover by inserting the tongue 79 into an opening 80 in the front wall 54 of the positioning rack 50. The projection 76 can pivot within the opening 80, but is retained within the opening by the tongue 79, thus preventing accidental detachment of the instrument retainer from the cassette. The projection 76 permits pivotal movement of the instrument retainer in three planes and thus allows the instrument retainer to lie down flat against the top wall 40, as shown in phantom in FIG. 1, so that it is out of the way during a procedure.

The retaining bar 72 is provided with an outwardly extending pin 82 at its other end for fastening the instrument retainer to the cover. The rear side wall 46 of the cover is provided with a fastening plate 84 (FIGS. 1 and 9) having upper and lower horizontal slots 86 and 88, respectively, which slidably receive the pin 82. Because the pin 82 slides easily into and out of the horizontal slot 86, the instrument retainer 70 can be manipulated with one hand to retain or release the instruments in the positioning rack 50. The fastening plate is provided with a hole 89 through which fastening means, such as a nut and bolt, may be inserted to mount the fastening plate on the rear side wall 46. The means used to mount the hinge mechanism 56 may be used to simultaneously mount the fastening plate.

The instrument retainer 70 can be alternately moved between a first position, shown in FIGS. 1-5, where the stem 77 of the J-shaped projection 76 overlies the front wall 54 of the instrument positioning rack 50 (in the open position) and the pin 82 is inserted into the upper slot 86, and a second inverted position, shown in FIGS. 6-7, where the tongue 79 overlies the front wall 54 of the instrument positioning rack (when the cassette is in the open position) and the pin 82 is inserted into the lower slot 88.

To position the instrument retainer 70 into the first position, the tongue 79 is inserted into the opening 80 in a direction from front to rear of the cassette and the instrument retainer is pivoted so that it lies transversely over the instruments in the positioning rack 50. The pin 82 is then inserted into the upper slot 86 to fasten the instrument retainer in place. The resilient retaining member 74 pressingly contacts the instruments in the upper positioning rack 50 and retains them in the grooves 32. As the cassette is closed, the resilient retaining member 74 also comes into pressing contact with the instruments in the lower positioning rack 30 to thereby simultaneously retain the instruments in both the upper and lower positioning racks, as shown in FIG. 4. In this first position, when the cassette is closed, the distance between the resilient retaining member 74 and the top wall 40 of the cover is approximately the same as the distance between the resilient retaining member and the bottom wall 16 of the tray, so that instruments of approximately the same diameter can be simultaneously retained in the upper and lower positioning racks.

To move the instrument retainer 70 into the second, inverted position shown in FIGS. 6-7, the tongue 79 is inserted into the opening 80 in a direction from rear to front of the cassette and the instrument retainer is pivoted so that the tongue overlies the front wall 54 of the positioning rack 50 and the instrument retainer 70, with its resilient member 74, lies in contact with the top wall 40. The pin 82 is then inserted into the lower slot 88 to fasten the instrument retainer in place. When the cassette is closed in this second position, the greater distance between the resilient member 74 and the bottom wall 16 permits the retention of larger instruments, such as forceps, elevators, and the like, in the lower positioning rack 30.

The particular length of the curved portion 78 and the particular location of the opening 80 are variable depending upon the shapes of the retaining bar and the resilient member. FIG. 10 shows an example of a variation illustrating the position of the instrument retainer when the resilient member is relatively thin. In this embodiment, the curved portion 78A of the hooked projection 76A is lengthened, and the opening 80A in the front wall 54 is moved closer to the top wall 40. The retaining bar 72 is thus positioned closer to the top wall 40, causing the resilient member to be in contact with the top wall in the inverted position.

The particular shapes of the retaining bar and the resilient retaining member are not critical to the invention. They can take many different forms, as long as the retaining bar provides support for the resilient retaining member transverse to the instruments, and as long as the resilient retaining member functions to pressingly contact the instruments in the retaining rack. FIG. 11 shows one alternative embodiment of the retaining bar and FIGS. 12-14 show one alternative embodiment of the resilient retaining member.

In FIG. 11, the alternative embodiment of the instrument retainer 118 includes a flat, rectangularly shaped retaining bar 120 having flat, L-shaped tabs 122 integrally formed at each end of the bar. The tabs 122 extend perpendicularly from the ends of the bar and lie in the same horizontal plane as the bar. The arms of each L-shaped tab extend toward each other to create a retaining space 124 adjacent each end of the retaining bar. The resilient hollow retaining member 74 is mounted on the retaining bar 120 so that the ends of the resilient retaining member fit into the retaining spaces 124 and are captured between the tabs 122 and the bar 120. The retaining bar 120 is provided at one end thereof with the projection 76 to pivotally mount the retaining bar to the cover. The pin 82 is provided at the other end thereof to fasten the instrument retainer 118 to the cover. The instrument retainer 118 functions in the same manner as the instrument retainer 70, illustrated in FIGS. 1-8, to retain instruments in the instrument cassette.

Turning now to FIGS. 12-14, another alternative embodiment of an instrument retainer 130 includes the retaining bar 72 and a resilient X-shaped retaining member 132 mounted on the retaining bar. The retaining bar is identical to that described in connection with FIGS. 1-8, and includes the rectangularly shaped slot 73.

The X-shaped retaining member 132 is formed from a flexible heat resistant material, such as silicone, and is preferably formed by extrusion. The retaining member includes two longitudinally extending notches 134 centrally positioned on each side of the retaining member. The notches 134 receive the sides of the retaining bar 72 when the retaining member 132 is inserted into the rectangularly shaped slot 73.

The retaining bar 72 includes the projection 76 to pivotally mount the retaining bar to the cassette cover, and the pin 82 to fasten the instrument retainer 130 to the cover. When the instrument retainer 130 is fastened to the cover and the cassette is in the closed position, the arms of the X-shaped retaining member 132 pressingly contact the instruments, as shown in FIG. 14, to retain the instruments in the positioning racks.

The invention disclosed herein may be embodied in other specific forms without departing from the spirit or central characteristics thereof. The embodiments described herein are therefore to be considered in all respects as illustrative and not restrictive, the scope of the invention being indicated by the appended claims, rather than by the foregoing description of the preferred embodiments, and all changes which come within the meaning and range of equivalency of the claims are intended to be embraced therein.

What is claimed is:

1. An instrument cassette for holding and sterilizing dental instruments comprising:
   a lower tray and an upper cover hingeably joined together for movement between an open position and a closed position;
   instrument positioning racks fastened to the tray and the cover for positioning the instruments in side-by-side relation within the tray and the cover; and
   instrument retaining means for releasably retaining instruments in the positioning rack in the cover, said retaining means comprising a retaining bar having means at a first end thereof for pivotally mounting the retaining bar to the cover for pivotal movement in at least two planes, means at a second end thereof for releasably fastening the retaining bar to the cover, and a resilient retaining member mounted on the retaining bar, the resilient retaining member pressingly contacting the instruments positioned in the positioning rack in the cover when the retaining bar is fastened to the cover to thereby retain the instruments in the positioning rack in the cover.

2. The instrument cassette according to claim 1 wherein the resilient retaining member pressingly contacting the instruments positioned in the positioning rack in the tray when the cassette is in the closed position, to thereby simultaneously retain the instruments in the positioning racks in the tray and the cover.

3. The instrument cassette according to claim 1 wherein the retaining means is removably pivotally mounted to the cover to permit adjustment of the instrument retaining means between a first instrument retaining position and a second, inverted instrument retaining position.

4. The instrument cassette according to claim 1 wherein the means for pivotally mounting the retaining bar comprises a hooked projection extending outwardly from the first end of the retaining bar.

5. The instrument cassette according to claim 1 wherein the means for fastening the bar comprises a pin extending outwardly from the second end of the bar, the pin being slidingly received within a horizontal slot on the cover.

6. The instrument cassette according to claim 1 wherein the retaining bar is formed of metallic material.

7. An instrument cassette for holding and sterilizing dental instruments comprising:
   a lower tray having a bottom and four tray sidewalls defining a tray interior;
   an upper cover having a top and four cover sidewalls defining a cover interior;
   a hinge positioned on a first tray sidewall and a first cover sidewall for hingeably joining the tray and the cover together for pivotal movement between an open position and a closed position;
   instrument positioning racks mounted within the tray interior and the cover interior for positioning the instruments in side-by-side relation within the tray and the cover;
   an instrument retainer removably mounted within the cover, the instrument retainer comprising a retaining bar having means at a first end thereof for pivotally mounting the instrument retainer within the cover for pivotal movement in at least two planes between a retaining position and a non-retaining position, and means at a second end thereof for releasably fastening the retaining bar to the cover, and a resilient retaining member mounted on the retaining bar, the resilient retaining member transversely pressingly contacting the instruments in the positioning racks in the tray and the cover when the cassette is in the closed position and the instrument retainer is in the retaining position to thereby retain the instruments in the positioning racks.

8. The cassette according to claim 7 further including a locking mechanism on a second tray sidewall opposite the first tray sidewall and on a second cover sidewall opposite the first cover sidewall for locking the cover to the tray in the closed position.

9. The cassette according to claim ,8 wherein the instrument positioning rack in the tray includes a front wall parallel to and spaced apart from the second tray sidewall, to provide space within the tray interior to hold auxiliary items.

10. The cassette according to claim 7 wherein the first cover sidewall includes a fastening plate mounted thereon in the cover interior, the fastening plate having means defining at least one horizontal slot, and wherein the releasable fastening means comprises a pin extending outwardly from the second end of the retaining bar and slidingly receivable within the horizontal slot.

11. The cassette according to claim 10 wherein the pivotal mounting means comprises a hooked projection extending outwardly from the first end of the retaining bar.

12. The cassette according to claim 11 wherein the hooked projection has a stem portion that projects outwardly from the first end of the retaining bar in a direction that is coaxial with a central longitudinal axis extending through the retaining bar, a curved portion that is perpendicular to the stem portion and co-planar with the stem portion and the central longitudinal axis, and a tongue portion that extends outwardly from the curved portion in a direction substantially perpendicular to the plane containing the central longitudinal axis and the stem portion.

13. The cassette according to claim 12 wherein the instrument positioning rack within the cover interior includes two opposed parallel sidewalls and a front wall, and the pivotal mounting means is mounted to the front wall.

14. The cassette according to claim 13, wherein the fastening plate has means defining two horizontal slots, one positioned above the other, and the instrument retainer is adjustable from a first position, wherein the stem portion of the pivotal mounting means overlies the front wall and the pin is received in one horizontal slot, to a second, inverted position, wherein the tongue portion overlies the front wall and the pin is received in the other horizontal slot.

15. The cassette according to claim 7, wherein the retaining bar is a flat, rectangularly shaped bar having means defining a rectangularly shaped slot therethrough, and the resilient retaining member is fitted within the slot and extends above and below the retaining bar to simultaneously pressingly contact the instruments in the instrument positioning racks when the cassette is in the closed position.

16. The cassette according to claim 7, wherein when the instrument retainer is in the non-retaining position, the instrument retainer lies flat against the top of the cover and is parallel to the instruments in the instrument positioning racks.

17. An instrument cassette for holding and sterilizing instruments comprising:
   a lower tray having a bottom and four tray sidewalls defining a tray interior;
   an upper cover having a top and four cover sidewalls defining a cover interior;
   a hinge positioned on a first tray sidewall and a first cover sidewall for hingeably joining the tray and the cover together for pivotal movement between an open position and a closed position;
   instrument positioning racks mounted within the tray interior and the cover interior for positioning the instruments in side-by-side relation within the tray and the cover;
   an instrument retainer removably mounted within the cover, the instrument retainer comprising a retaining bar having means at a first end thereof for pivotally mounting the instrument retainer within the cover for pivotal movement in at least two planes between a retaining position and a non-retaining position, the pivotal mounting means comprising a hooked projection having a stem portion that projects outwardly from the first end of the retaining bar in a direction that is coaxial with a central longitudinal axis extending through the retaining bar, a curved portion that is perpendicular to the stem portion and co-planar with the stem portion and the central longitudinal axis, and a tongue portion that extends outwardly from the curved portion in a direction substantially perpendicular to a plane containing the central longitudinal axis and the stem portion, the retaining bar further having means at a second end thereof for releasably fastening the retaining bar to the cover, and a resilient retaining member mounted on the retaining bar, the resilient retaining member transversely pressingly contacting the instruments in the positioning racks in the tray and the cover when the cassette is in the closed position and the instrument retainer is in the retaining position to thereby retain the instruments in the positioning racks.

18. The cassette, according to claim 17, wherein when the instrument retainer is in the non-retaining position, the instrument retainer lies flat against the top of the cover and is parallel to the instruments in the instrument positioning racks.

19. An instrument cassette for holding and sterilizing instruments comprising:
   (a) a lower tray and an upper cover hingeably joined together for movement between an open position and a closed position;
   (b) instrument positioning racks fastened to the tray and the cover for positioning the instruments in side-by-side relation within the tray and the cover;
   (c) an instrument retainer removably mounted within the cover and adjustable between a first position and a second, inverted position, the instrument retainer comprising
      a retaining bar having means at a first end thereof for pivotally mounting the retaining bar to the cover, and means at a second end thereof for releasably fastening the retaining bar to the cover, and a resilient retaining member mounted on the retaining bar, the pivotal mounting means being releasable from the cover to permit adjustment of the instrument retainer from the first position to the second, inverted position;
   (d) means for slidably receiving the fastening means in the first and second position comprising respective upper and lower slots;
   whereby when the instrument retainer is in the first position, it pressingly contacts the instruments positioned in the positioning racks in the tray and the cover when the cassette is in the closed position, and when the instrument retainer is in the second position, it pressingly contacts the instruments positioned in the positioning rack in the tray and contacts the cover when the cassette in the closed position.

* * * * *